(12) United States Patent
Cheung et al.

(10) Patent No.: US 7,695,471 B2
(45) Date of Patent: Apr. 13, 2010

(54) FIXATION DEVICE

(75) Inventors: Kenneth M. C. Cheung, Hong Kong (CN); Kelvin W. K. Yeung, Hong Kong (CN); Tak-Lun Poon, Hong Kong (CN); Shew-Ping Chow, Hong Kong (CN); William Weijia Lu, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 986 days.

(21) Appl. No.: 10/827,664

(22) Filed: Apr. 19, 2004

(65) Prior Publication Data

US 2004/0230193 A1    Nov. 18, 2004

Related U.S. Application Data

(60) Provisional application No. 60/464,082, filed on Apr. 18, 2003, provisional application No. 60/464,083, filed on Apr. 18, 2003.

(51) Int. Cl.
*A61B 17/58* (2006.01)
(52) U.S. Cl. .......................................... 606/63; 606/78
(58) Field of Classification Search ............ 606/62–64, 606/78, 362, 327
See application file for complete search history.

(56) References Cited

U.S. PATENT DOCUMENTS

| | | | |
|---|---|---|---|
| 4,170,990 A | | 10/1979 | Baumgart |
| 4,485,816 A | * | 12/1984 | Krumme ..................... 606/219 |
| 5,358,405 A | * | 10/1994 | Imai ............................ 433/215 |
| 5,474,557 A | * | 12/1995 | Mai ............................. 606/78 |
| 5,586,983 A | * | 12/1996 | Sanders et al. ................ 606/61 |
| 5,758,713 A | * | 6/1998 | Fallet .......................... 164/404 |
| 6,127,597 A | | 10/2000 | Beyar |
| 6,200,330 B1 | * | 3/2001 | Benderev et al. ............ 606/232 |
| 6,224,600 B1 | | 5/2001 | Protogirou |
| 6,235,031 B1 | | 5/2001 | Hodgeman |
| 6,261,289 B1 | * | 7/2001 | Levy .......................... 606/63 |
| 6,306,141 B1 | | 10/2001 | Jervis |
| 6,332,885 B1 | * | 12/2001 | Martella ...................... 606/78 |
| 6,554,833 B2 | * | 4/2003 | Levy et al. ................... 606/63 |

FOREIGN PATENT DOCUMENTS

JP         01310664         6/1988

OTHER PUBLICATIONS

Gil et al., "Relevant aspects in the clinical applications of NiTi shape memory alloys," Journal of Materials Science: Materials in Medicine, vol. 7, pp. 403-406 (1996).

(Continued)

*Primary Examiner*—Thomas C Barrett
*Assistant Examiner*—Michael J Araj
(74) *Attorney, Agent, or Firm*—Cohen Pontani Lieberman Pavane LLP

(57) ABSTRACT

The present invention relates to a bone fixation device having a fixation member using a shape memory effect to secure bone fractures, including but not limited to, femur, tibia and humerus fractures. The fixation member can be malleable at a room temperature, but become rigid at a body temperature because of the shape memory effect, such as derived from a super-elastic property found in such as a nickel titanium alloy. The fixation member can be formed on one or more of the shaft portion and the two end portions of a nail member for securing bone fractures, such as by providing translational and rotational stabilities. The fixation member is also capable of providing a continuous and controllable compression force over the fractured bone, if needed.

22 Claims, 7 Drawing Sheets

OTHER PUBLICATIONS

Miyazaki et al., "Effect of Thermal Cycling on the Transformation Temperatures of Ti-Ni Alloys," Acta metall., vol. 34, pp. 2045-2051 (1986).

Liu et al., "Criteria of Transformation Sequences in NiTi Shape Memory Alloys," Materials Transactions, JIM, vol. 37, pp. 691-696 (1996).

Sadrnezhaad et al., "Heat Treatment of Ni-Ti Alloy for Improvement of Shape Memory Effect," Materials and Manufacturing Processes, vol. 12, pp. 107-115 (1997).

Liu et al., Journal of Materials Science, vol. 32, pp. 5979-5984 (1997).

T. Saburi, "Ti-Ni shape memory alloys", Shape Memory Materials, Cambridge University Press, pp. 49-96 (1999).

Gil et al., "Thermal Cycling and Ageing Effects in Ni-Ti Shape Memory Alloys Used in Biomedical Applications", 11th Conference of the ESB, Toulouse, France (Jul. 1998).

* cited by examiner

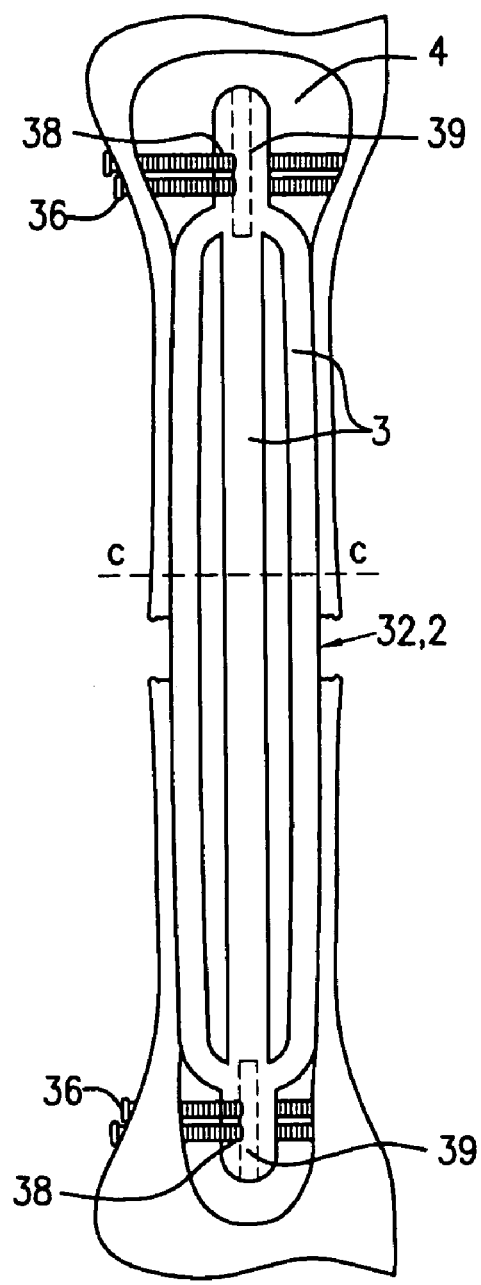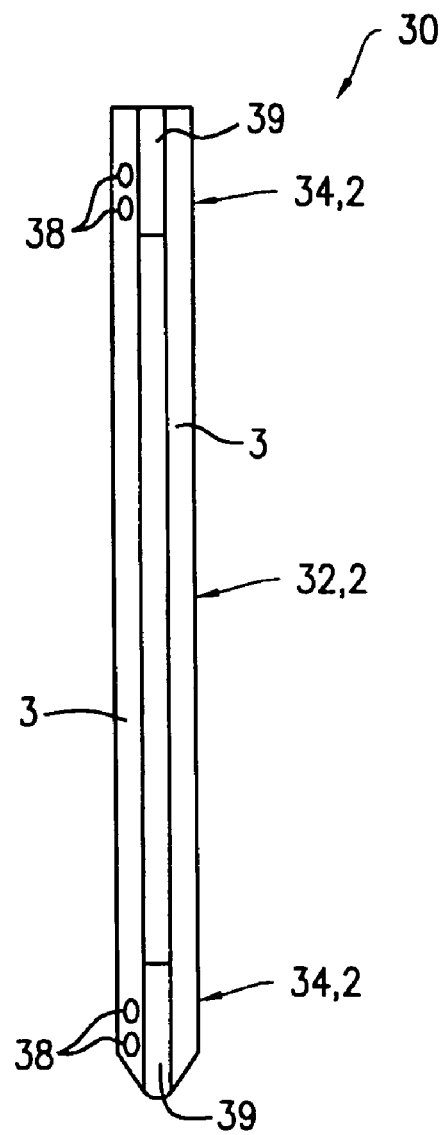
FIG. 3a
FIG. 3b

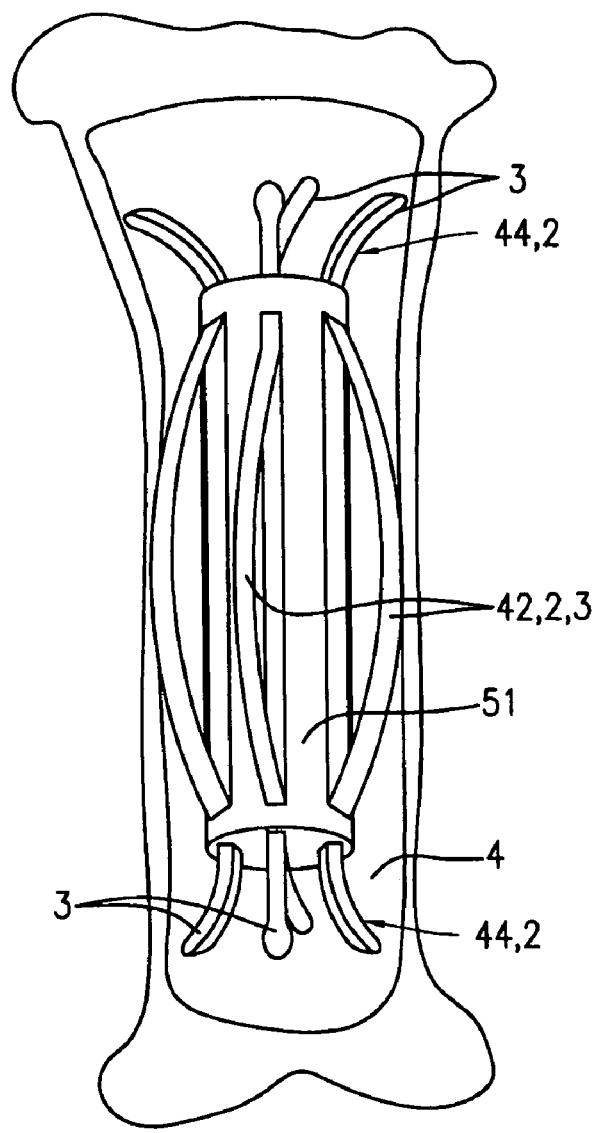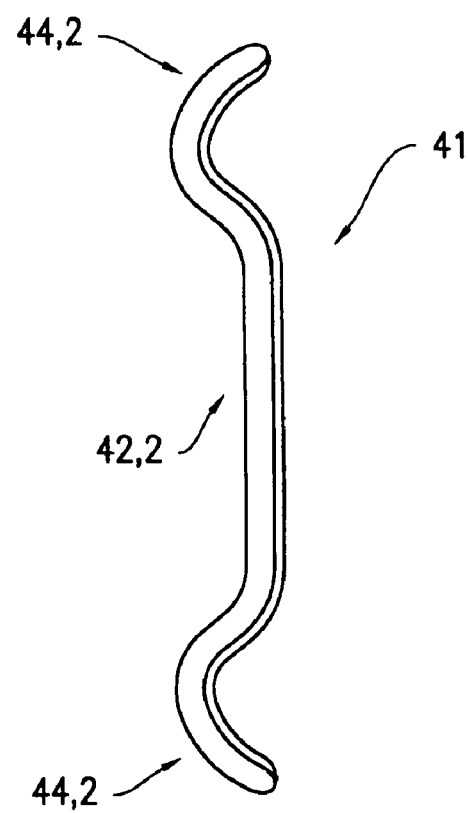
FIG. 4a
FIG. 4b

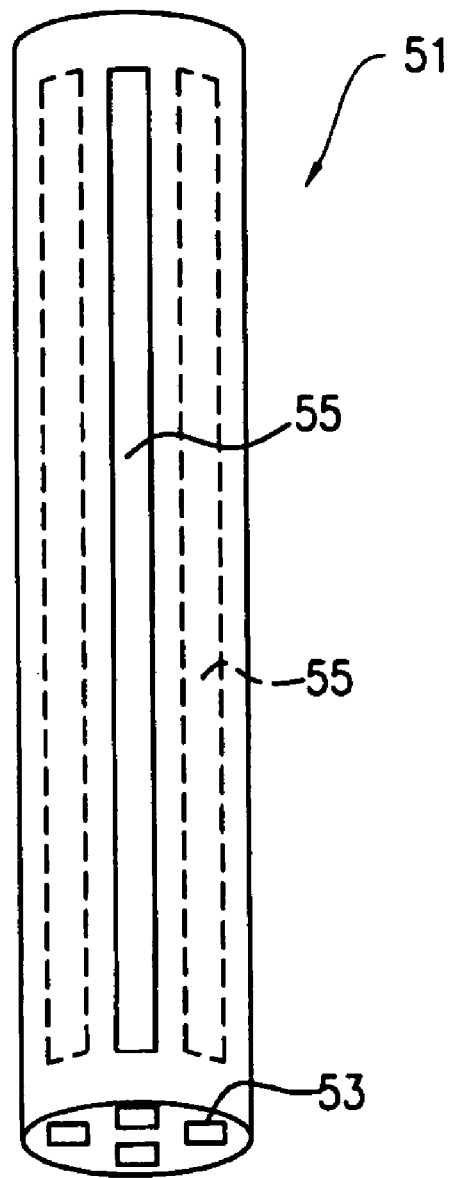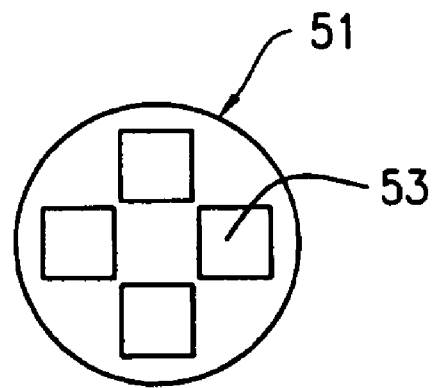
FIG. 4d
FIG. 4c

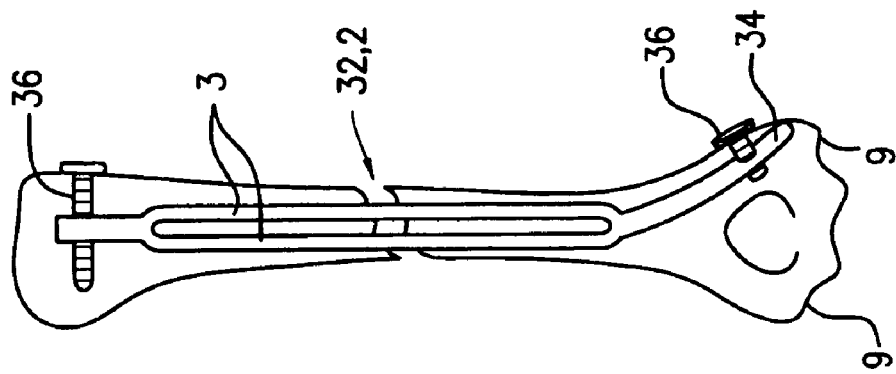
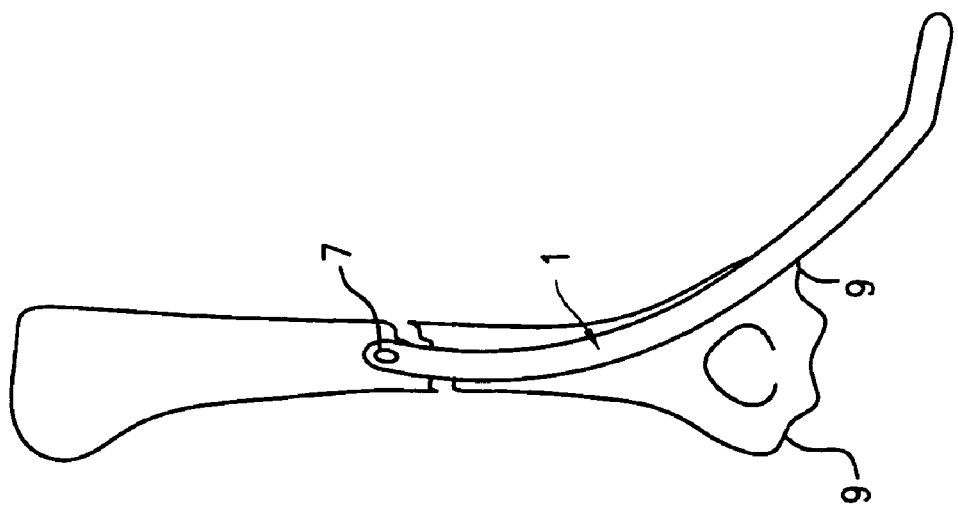
FIG. 5a
FIG. 5b

FIXATION DEVICE

CROSS-REFERENCE TO RELATED APPLICATION

This application claims the benefit of U.S. Provisional Patent Application Nos. 60/464,082 and 60/464,083 both filed Apr. 18, 2003.

FIELD OF THE INVENTION

The present invention relates generally to a fixation device and a fixation member, such as a bone fixation implant. In particular, the present invention relates to an intramedullary fixation device using super-elasticity and/or shape memory effect for bone fracture fixation. The present invention also relates to a method of fixing bone fractures.

BACKGROUND OF THE INVENTION

Various fracture fixation devices have been used to treat bone fractures. For example, intramedullary (IM) nailing devices are used for long bone shaft fractures. IM nail members such as reamed or un-reamed nail members can be combined with or without interlocking screws to secure the nail members in position. For example, shaft fractures with significant soft-tissue injuries can be treated using IM nail members which were inserted without reaming.

Conventional fixation devices are associated with various biomechanical problems. For example, reamed nail members can cause damages to the internal cortical blood supply since the medullary cavity has been reamed. Un-reamed nail members typically have a smaller diameter for easy insertion and consequently have loose fittings. Apart from the local damage, some changes such as pulmonary embolization, temperature-related changes of the coagulation system and humoral, neural and inflammatory reactions are to be considered. Moreover, due to the anatomical structures of tibia and humerus, current IM nailing devices cannot repair long bone fractures satisfactorily. Additionally, the entry point at the humerus presents a difficult problem.

The present invention provides a bone fixation device and a fixation member capable of reducing surgical trauma at the time of insertion. Additionally or alternatively, the present invention provides a bone fixation device and a fixation member capable of facilitating faster healing of and providing improved biomechanical properties to the fractured bone during healing.

SUMMARY OF THE INVENTION

The present invention employs the shape memory effect to fix bone fractures without using other fastening elements. More specifically, the present invention provides a fixation member variable between a retracted shape and an expanded shape. When the fixation member is in its retracted shape, the fixation member can freely move about a fractured bone portion. When the fixation member is in its expanded shape, the fixation member can join to the fractured bone portion and be mounted thereonto.

According to another aspect of the present invention, a bone fixation method is provided, which can comprise providing a bone fixation member variable between a retracted shape and an expanded shape. When the bone fixation member is in a retracted shape, the bone fixation member is placed in a predetermined position for fixing a fractured bone portion. When the bone fixation member turns into its expanded shape, the bone fixation member mounts onto the fractured bone portion for bone fixation.

BRIEF DESCRIPTION OF THE DRAWINGS

The detailed description of the present invention will be better understood in conjunction with the accompanying drawings. Nevertheless, the accompanying drawings are for illustrative purposes only; the present invention is not limited to the exemplary embodiments shown in such drawings.

FIG. 1 depicts a first embodiment of the fixation device, in which

FIG. 2 depicts a second embodiment of the fixation device, in which

FIG. 3 depicts a third embodiment of the fixation device, in which FIG. 3a shows an exemplary fixation device after joining to a bone portion at a body temperature state; FIG. 3b shows an exemplary nail member at a cold temperature.

FIG. 4 depicts a fourth embodiment of the fixation device, in which FIG. 4a shows an exemplary fixation device after joining to a bone portion; FIG. 4b is a perspective view of an exemplary nail member; FIG. 4c is a perspective view of an exemplary support member; and FIG. 4d is an end view of the support member shown in FIG. 4c.

FIG. 5 depicts an exemplary bone fixation device being applied to secure a humerus fracture, in which FIG. 5a illustrates the nail member insertion at olecranon fossa and FIG. 5b illustrates the expansion of the fixation member after the insertion.

DETAILED DESCRIPTION OF THE INVENTION

Figure 1B:
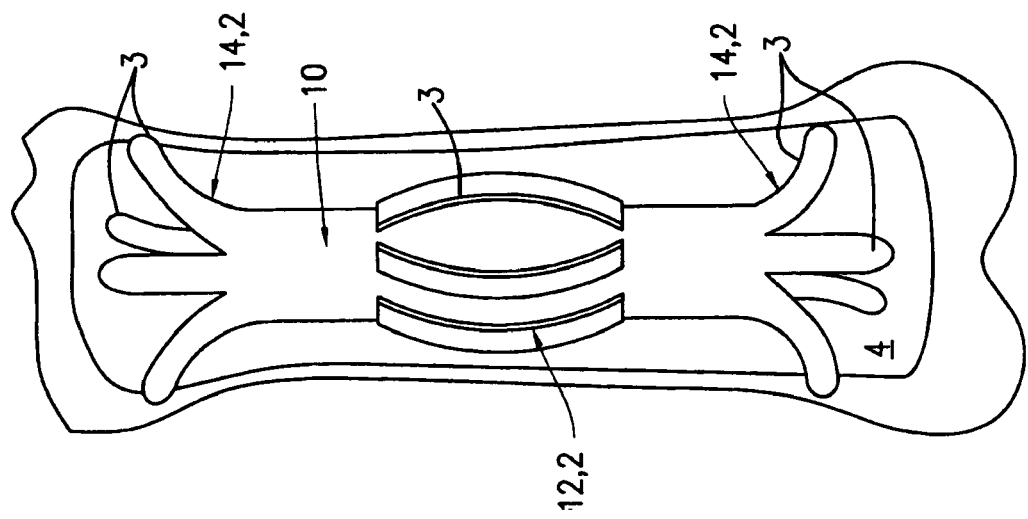
FIG. 1a shows an exemplary nail member at a cold temperature state and FIG. 1b shows an exemplary fixation device after joining to a bone portion at a body temperature.

Exemplary fixation members, devices, and methods embodying the principles of the present invention are shown throughout the drawings.

The present invention can provide equilibrium forces for use in various bone fracture fixation. In one embodiment, the equilibrium forces can be derived from a super-elastic or pseudo-elastic property, such as found in a shape memory material. Additionally or alternatively, the present invention can provide a bone fracture fixation member, device and method capable of reducing surgical trauma at the time of insertion.

More specifically, the present invention employs the shape memory effect and/or super-elasticity or pseudo-elasticity in the application of bone fixation. For example, such shape memory effect can be found in a shape memory material, such as a nickel-titanium alloy material. The shape memory property means that the shape of the structural component can change upon a temperature change. In an exemplary embodiment, the shape memory material can be subjected to a predetermined thermo-mechanical treatment. There can be a one-way-shape-memory or two-way-shape-memory. In case of a two-way-shape-memory, the shape change is reversible upon the return of the temperature. Additionally or alternatively, super-elasticity or pseudo-elasticity can refer to a property of a material that can produce a constant and continuous force while being deformed or relaxing from deformation. In one exemplary embodiment, a super-elastic or pseudo-elastic material can afford a constant force or similar forces when such a material is being mechanically or physically deformed beyond its elastic limit but within its plastic limit. Such a force can be kept constant or substantially constant during that range of deformation.

A shape memory or super-elastic material is described in a co-pending patent application entitled "Shape Memory Material And Method Of Making The Same" filed concurrently herewith by K. M. C. Cheung, K. W. K. Yeung, W. W. Lu and J. C. Y. Chung, the disclosure of which is incorporated herein by reference.

According to another aspect of the present invention, a fixation device 1 can be provided which can comprise a fixation member 2 capable of affording equilibrium forces for bone fixation. In particular, such equilibrium forces can be provided without the use of additional fixation mechanism. For example, the fixation member 2 can be formed to employ the shape memory effect. In one exemplary embodiment, the fixation member 2 can comprise a super-elastic or pseudo-elastic material or other materials having a shape memory property. In an exemplary embodiment, the fixation member 2 can be formed of a nickel titanium alloy. In anther exemplary embodiment, the fixation member 2 can be formed of a shape memory and/or super-elastic material such as described in the above referenced co-pending application.

According to a further aspect of the present invention, a fixation device 1 can be provided which can comprise a fixation member 2 capable of anchoring onto or otherwise joining to a bone portion for bone fixation. For example, the fixation member 2 can join to an inner bone canal 4. In particular, the fixation member 2 can anchor or join to the bone portion without the use of additional fixation mechanism. In one embodiment, the fixation member 2 is variable between a first shape and a second shape. When being in the first shape, the fixation member can freely move about a bone portion. When being in the second shape, the fixation member can join to the bone portion and be affixed thereonto for bone fixation. For example, the fixation member can be affixed the bone portion so that the fixation device 1 can be mounted onto the bone portion without additional fixation mechanism.

In one exemplary embodiment, the fixation member 2 can be made of a super-elastic or pseudo-elastic material or other materials with a shape memory property. The fixation member 2 can be subjected to a predetermined thermo-mechanical treatment. In an exemplary embodiment, the phase transformation of the fixation member 2 from martensitic phase to austenitic phase can result in an expansion of the fixation member 2. For example, the fixation member 2 can expand to join to a bone portion, thereby securing the fractured bone portion. In an exemplary embodiment, the fixation member 2 can change its shape at a body temperature. In another exemplary embodiment, the phase transformation of the fixation member 2 from austenitic phase to martensitic phase can result in contracting of the fixation member 2, such as to facilitate the removal of the fixation member 2 from the canal 4. The fixation member 2 can change its shape by heating or by gradual warming through various natural means such as body heat.

The fixation member 2 can be in various forms. In an exemplary embodiment, the fixation member 2 can comprise one or more section elements 3, such as shown in the various drawings. The section elements 3 can be adapted to join to a bone portion and mount the fixation member 2 onto the bone portion. In an exemplary embodiment, the section elements 3 can be formed on an extreme portion of a structural component where the section elements 3 can extend freely. For example, the section element 3 can be formed at an end portion 14 of a nail member 10, such as shown in FIG. 1b. In another exemplary embodiment, the section members 3 can be formed in a middle portion of a structural component. For example, the section members 3 can be formed in a shaft portion of a nail member, such as shown in FIG. 1b.

Figure 1A:
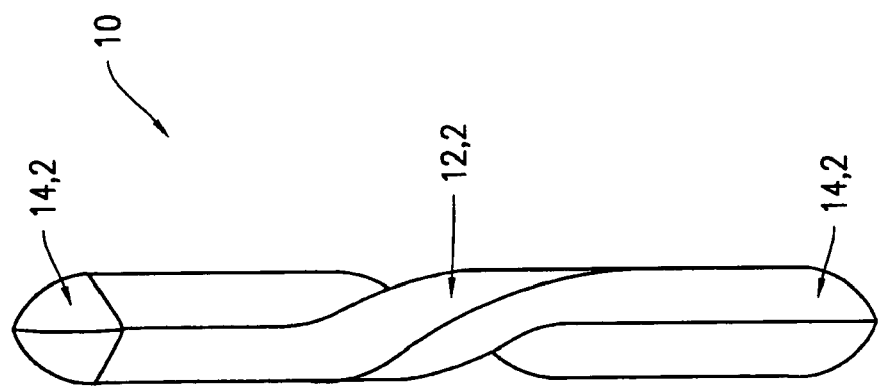

The section elements 3 can change between a first shape and a second shape. For example, the section elements 3 can change from a retracted shape, such as shown in FIG. 1a, to an expanded shape, such as shown in FIG. 1b. In an exemplary embodiment, the section elements 3 can remain in a retracted shape, such as at a room temperature. In anther exemplary embodiment, the section elements 3 can expand in a transverse direction of a bone portion, such as shown in FIG. 1b, when the temperature is increased to close to an average body temperature. In another exemplary embodiment, the section elements 3 can become stiff or rigid when they change into an expanded shape to engage the bone portion and affix the fixation member 2 to such bone portion. In an exemplary embodiment, the expanded section elements 3 can securely join to a bone portion and restrict the fixation member 2 from undesired movement in relation to the bone portion.

Figure 2B:
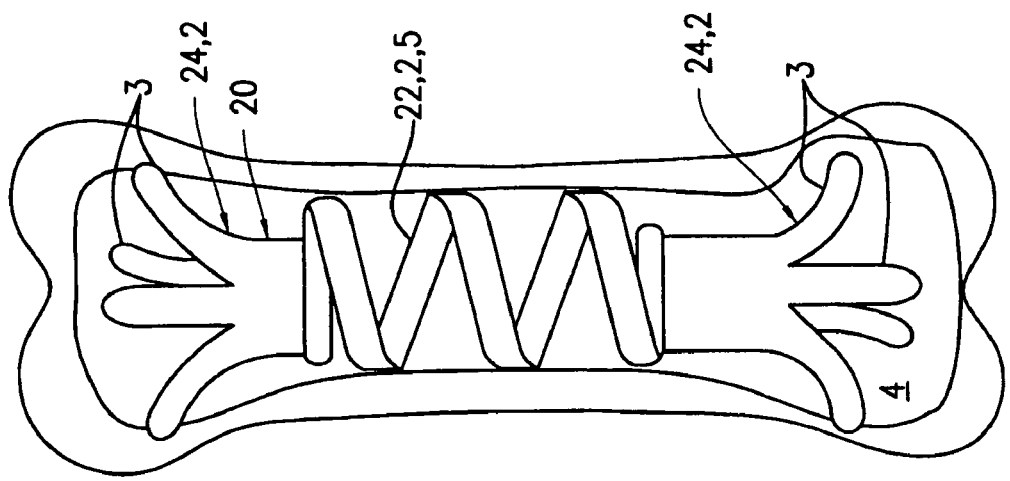
FIG. 2a shows an exemplary nail member at a cold temperature state and FIG. 2b shows an exemplary fixation device after joining to a bone portion at a body temperature.

In another exemplary embodiment, the fixation member 2 can be in the form of a spring coil 5, such as shown in FIG. 2. In an exemplary embodiment, the spring coil 5 can expand in a transverse direction of a bone portion, such as shown in FIG. 2b. In another exemplary embodiment, the spring coil 5 can expand in a longitudinal direction of a bone portion, such as shown in FIG. 2b. In a further exemplary embodiment, the spring coil 5 can expand in both longitudinal and transverse direction of a bone portion, such as shown in FIG. 2b. It will be appreciated that various other embodiments of the fixation member 2 are also within the scope of the present invention.

In another exemplary embodiment, the fixation device 1 can be formed with a nail member 10, 20, 30, or 40, such as shown in the various drawings, each of the nail member having a shaft portion and two end portions. For example, the fixation member 2 can be formed on one or more of the shaft and end portions of the nail member. In an exemplary embodiment, such as shown in FIG. 1, the nail member 10 can have built-in flexible and expandable fixation members 2 formed on the end portions 14. Such fixation members 2 can function as anchors for joining to a bone portion, without using additional fasteners, such as locking screws. These anchors can expand in response to the ambient temperature change to a body temperature after the nail member 10 is inserted into the medullary canal 4. The fixation members 2 are capable of producing a rigid fixation force over the entire length of the bone port to prevent axial rotation, angular bending moment, and transverse and longitudinal translations of the fractured bone after the fixation members 2 expand. It will be appreciated that other embodiments of the fixation device 1 and the fixation member 2 are also within the scope of the present invention.

Additionally or alternatively, the fixation device 1 can be formed so as to apply intraosseous forces over a fractured bone to facilitate a rapid healing. For example, the fixation members 2 are capable of providing a continuous and controllable compression force established at a fracture site, thereby achieving a faster healing. In an exemplary embodiment, the fixation members 2 formed at the end portions of a nail member are capable of pulling the two fractured bone sections toward each other, thereby providing a compression force to the fractured bone ends. In another exemplary embodiment where the fixation members 2 expand in a traverse direction of the nail member, the nail member can contract in the longitudinal direction.

According to a further aspect of the present invention, the fixation member 2 is capable of being implanted in a predetermined position for bone fixation with a minimum surgical trauma. For example, the fixation member 2 can remain a malleable state prior to insertion. Such a fixation member 2 can be easily manipulated to a desired shape to facilitate the insertion. In an exemplary embodiment, the fixation member 2 can remain in a malleable state, such as at a room temperature, before insertion.

In one exemplary embodiment, the fixation member 2 can comprise a super-elastic or pseudo-elastic material or other materials having a shape memory property. In an exemplary embodiment, the operative physical properties of the fixation member 2 can be malleability at a room temperature, and rigidity at a body temperature. In another exemplary embodiment, the fixation member 2, in its flexible or malleable state, can be easily manipulated and/or inserted into a medullary canal 4. After the fixation member 2 is inserted and warmed up to a body temperature, the fixation member 2 can become stiff or rigid to maintain a fixed position for bone fixation. In one exemplary embodiment, the fixation member 2 can expand as being warmed to the body temperature. The expanded fixation member 2 is capable of securing to the fractured bone and/or providing compression to the fractured bone ends, if necessary. Such an implant can provide faster healing and improved biomechanical properties of bone during healing.

In an exemplary embodiment, the fixation member 2 can be used for long bone internal fracture fixation. The property of flexibility and expandability of the fixation member 2, as well as the nail member, can facilitate the insertion of a humeral fixation device 1 or fixation member 2. The insertion can be carried out through the epicondyle 7 with minimum surgical trauma while the fixation member 2 is still in a retracted shape and malleable state and pushed into the humerus retrogradely through a cavity on either side of the olecranon fossa 9 into the shaft. When the fixation member 2 is seated in the shaft, the fixation member 2 can expand to anchor onto the shaft. It will be appreciated that other embodiments of using the fixation device 1 or fixation member 2 are also within the scope of the present invention.

The fixation device 1 as well as the fixation member 2 will now be described in great details through various exemplary embodiments and the accompanying drawings.

In one exemplary embodiment, such as shown in FIG. 1, the fixation device 1 can comprise a single-nail member 10 formed in various manners. For example, the nail member 10 can assume an elongated shape, in a cold temperature state, such as shown in FIG. 1a. In an exemplary embodiment, the nail member 10 can comprise a shaft portion 12 and two end portions 14. The shaft portion 12 can have various shapes, such as a rod, or cylindrical shape, and/or various cross-sectional shapes, such as triangular, square, hexagonal, or other shapes, or a combination of above shapes. In an exemplary embodiment, the shaft portion 12 can be in a twisted shape, such as shown in FIG. 1a. In another exemplary embodiment, the two end portions 14 can be spaced apart from each other by the shaft portion 12. In an exemplary embodiment, the two end portions 14 of the nail member 10 can be in various shapes, such as cone, pyramid, or other pointed shapes. It will be appreciated that other embodiments of the nail member 10 are also within the scope of the present invention.

The fixation device 1 can be formed in various manners. In an exemplary embodiment, one or more of the shaft portion 12 and the two end portions 14 can be formed as a fixation member 2. In an exemplary embodiment, the two end portions 14 can be formed as fixation members 2, such as described above. For example, the shaft portion 12 can be formed as one or more expandable elements 3, which is capable of changing between a retracted shape and an expanded shape. In an exemplary embodiment, such as shown in FIG. 1a, the fixation member 2 formed on the shaft portion 12 can be hidden by twisting the nail member 10 at the cold temperature state. In a further exemplary embodiment, at least a portion of the nail member 10 can be formed of a shape memory material as discussed above. In an exemplary embodiment, the entire nail member 10 can be made of a shape memory material.

In one embodiment, the fixation device 1 and the nail member 10 can change between a first shape and a second shape. In an exemplary embodiment, such as shown in FIG. 1a, the nail member 10 in a cold temperature state can assume a retracted shape. In another exemplary embodiment, the nail member 10 can assume an expanded shape. For example, one or more fixation members 2 on the nail member 10 can expand to mount the nail member 10 onto the walls of an intra-medullary canal 4, such as shown in FIG. 1b. In an exemplary embodiment, the expanded elements 3 formed on the end portions 14 of the nail member 10 can affix the fixation device 1 onto the bone portion to prevent the fixation device 1 from undesired movement in relation to the bone portion. In another exemplary embodiment, the fixation device 1 can be secured onto the bone portion without using additional fastening elements.

Additionally or alternatively, the fixation device 1 and/or the nail member 10 can change from a malleable and/or flexible state to a stiff or rigid state. In one exemplary embodiment, the entire nail member 10 can be made of a shape memory material. In an exemplary embodiment, the nail member 10 in the cold temperature state can be malleable, flexible, or otherwise be easily manipulated. For example, the nail member 10 can be bent to conform to a bone portion, such as by hand. In another exemplary embodiment, such as shown in FIG. 1a, the nail member 10 can assume a retracted shape. In a further exemplary embodiment, such as shown in FIG. 1b, the nail member 10 can turn into a rigid state, such as after being placed in a predetermined position and changing into an expanded shape. For example, the nail member 10 can change into a rigid state after being warmed to a predetermined temperature, such as an average body temperature. The rigid state of the nail member 10 can maintain the expanded shape and/or secure the nail member 10 in position.

The fixation device 1 or nail member 10 can be applied to secure various bone fractures, such as a long bone fracture. In one exemplary embodiment, the nail member 10 in a cold temperature state can be firstly introduced to an intra-medullary canal 4 using various techniques, such as an antegrade or a retrograde technique. When being in its cold temperature state, the nail member 10 can be manipulated to assume a predetermined shape and/or be placed inside the intra-medullary canal 4.

Additionally or alternatively, when the nail member 10 is warmed up to the body temperature after insertion, one or more of the fixation members 2 formed on the shaft portion 12 and/or two end portions 14 of the nail member 10 can then change to an expanded shape. For example, the shaft portion 12 and/or the two end portions 14 can expand outward until they catch the wall of intra-medullary canal 4. The expanded portions are capable of securing the nail member 10 at a predetermined position. If desired, other fastening members, such as lock screws, pins, or wires or the like can be used to provide additional fixation. It will be appreciated that other applications of the fixation device 1 are also within the scope of the present invention.

Figure 2A:
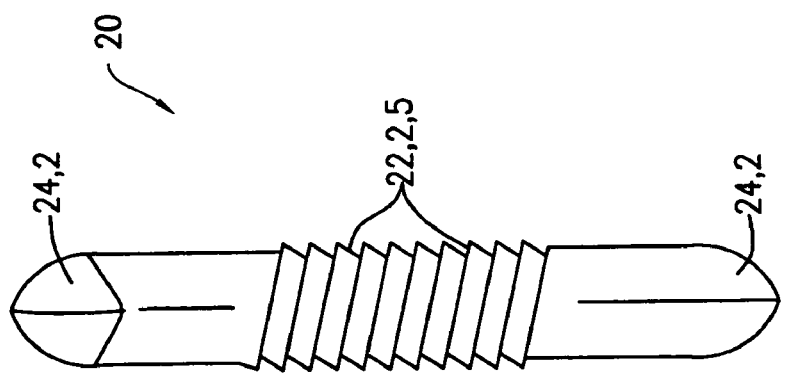

In another exemplary embodiment, such as shown in FIG. 2a, the fixation device 1 can comprise a single-nail member 20 similar to that described above. For example, the nail member 20 can comprise a shaft portion 22 and two end portions 24. In an exemplary embodiment, one or more of the shaft portion 22 and two end portions 24 can be formed as fixation member(s) 2. In an exemplary embodiment, such as shown in FIG. 2b, the fixation member 2 formed on the shaft portion 22 can be in the form of a spring coil 5. For example, the spring coil 5 can assume a contracted shape at a cold temperature state, such as shown in FIG. 2a. In another exemplary embodiment, the spring coil 5 can assume an extended shape, such as shown in FIG. 2b.

The nail member 20 at cold temperature state can be introduced into the intra-medullary canal 4 using an antegrade or a retrograde technique. When the nail member 20 is warmed up to the body temperature after insertion, the fixation member 2 formed at each of the two end portions 16 and/or the spring coil 5 can expand outward until they catch the wall of inner canal 4. Additionally or alternatively, the spring coil 5 can also extend its length in a longitudinal dissection of the nail member 20 until the nail member 20 is fixed in position. The fixation members 2 are capable of securing the nail member 20 at the desired position. If desired, other fasteners such as lock screw, pin, or wire can be used to provide additional fixation.

In a further exemplary embodiment, such as shown in FIG. 3a, the fixation device 1 can comprise a single-nail member 30. Similar to those described above, the nail member 30 can comprise a shaft portion 32 and two end portions 34. In one exemplary embodiment, the shaft portion 32 of the nail member 30 can be formed as a fixation member 2, such as in the form of expandable elements 3. For example, the shaft portion 32 can change between a retracted shape and an expanded shape, such as in response to a temperature change. In another exemplary embodiment, the two end portions 34 of the nail member 30 can be in various shapes, such as cone, pyramid, or other shapes. FIG. 3b illustrates an exemplary nail member 30 in a retracted shape.

The fixation device 1 and/or the nail member 30 at a cold temperature state can be introduced initially into the intra-medullary canal 4, such as using an antegrade or a retrograde technique. When the nail member 30 is warmed up to the body temperature after insertion, the fixation member 2 on the nail member 30 can expand outwardly, such as shown in FIG. 3a. The expanded fixation member 2 is capable of engaging anchors and/or securing the nail member 30 at the desired position.

Figure 3C:
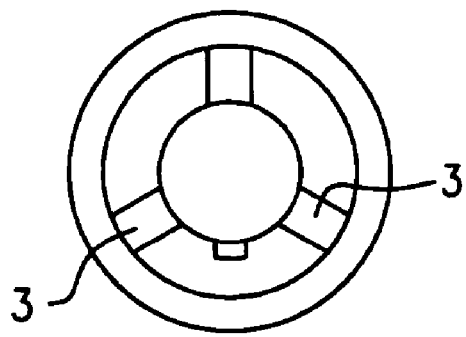
FIG. 3c to FIG. 3e show exemplary cross-sectional shapes of the fixation member.
Figure 3D:
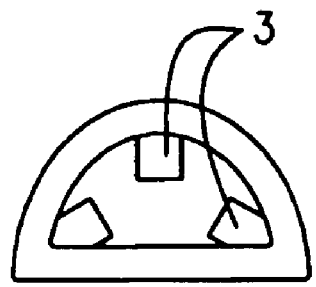
Figure 3E:
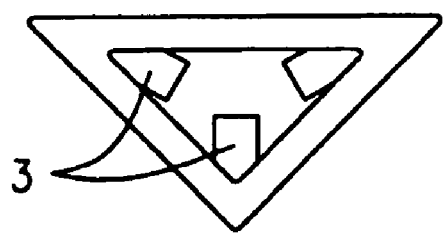

The fixation member 2 on the shaft portion 32 can be formed in various shapes. For example, the fixation member 2 can be so shaped that the fixation device 1 and/or the nail member 30 can be secured a bone portion of a particular shape. Exemplary cross-sectional shapes of the fixation members 2 are shown in FIG. 3c to FIG. 3e. In an exemplary embodiment, the fixation member 2 can comprise a plurality of section elements 3. For example, three expandable elements 3 can be provided. In one exemplary embodiment, three expandable elements 3 can be oriented to have about 120° between two adjacent elements 3. In an exemplary embodiment, the expandable elements 3 can be formed to expand in the shape as shown in FIG. 3c for securing a femur. In another exemplary embodiment, such as shown in FIG. 3d, the expandable elements 3 can be formed to fix a tibia. In a further exemplary embodiment, such as shown in FIG. 3e, the expandable elements 3 can be shaped to fix a humerus. It will be appreciated that various other embodiments of the expandable elements 3 are also within the scope of the present invention.

Additionally or alternatively, one or more fastening members 36 can be provided to afford additional fixation. For example, a plurality of interlocking screws 36 can be used to secure a long bone fracture. In an exemplary embodiment, at least one interlocking screw thread 38 can be provided at an end portion 34 of the nail member 30 to engage with the interlocking screws 36. In another exemplary embodiment, the fastening members 36 can be aligned in collinear, perpendicular to each other, or in other manners. Other fastening members, such as pins, wires, or the like can also be used to provide additional fixation.

Optionally, the fixation device 1 can be provided with additional structures 39 to facilitate the insertion and removal of the fixation device 1. In an exemplary embodiment, a longitudinal inter-nail member canal 39 can be provided at least one end portion 34. In another exemplary embodiment, the nail member canal 39 can allow inserting materials into the fixation device 1 to restore the nail member 30 to the cold temperature state during nail member removal.

In a further exemplary embodiment, such as shown in FIG. 4a, the fixation device 1 can be in the form of a nail-tube assembly 40, which can comprise one or more nail sections 41 and a support member 51. Each nail section 41 can be made of various materials, In another exemplary embodiment, at least a portion of the nail section 41 can be made of a shape memory material, such as that described above.

The nail section 41 can be formed in various shapes. In an exemplary embodiment, the nail section 41 can comprise a shaft portion 42 and two end portions 44, such as shown in FIG. 4b. In another exemplary embodiment, the nail section 41 can have at least one contoured fixation member 2 on the shaft portion 42. The two end portions 44 of the shaft portion 42 can have various shapes, such as cone or pyramid or other pointed shapes.

In an exemplary embodiment, such as shown in FIG. 4c, the support member 51 can be provided to assemble with one or more nail sections 41. The support member 51 can be formed in various shapes and sizes. For example, the support member 51 can be adapted to fit in an intra-medullary canal 4. In an exemplary embodiment, the support member 51 can have substantially cylindrical shape. In another exemplary embodiment, the support member 51 can be formed of various materials, such as metals, alloys or elastic materials such as PE.

In an exemplary embodiment, such as shown in FIG. 4d, the support member 51 can be provided with one or more chamber portions 53. For example, each chamber portion 53 can be adapted to extend longitudinally through the support member 51. In an exemplary embodiment, each chamber portion 53 can be formed to allow a nail section 41 to pass therethrough. In another exemplary embodiment, the chamber portions 53 can be adapted to accommodate and/or support the nail sections 41 after the nail-tube assembly 40 is formed. The chamber portions 53 can have various transverse section, such as circular, square, rectangular, hexagonal, or some other shapes. In an exemplary embodiment, each chamber portion 53 can have a cross-section complementary to that of the nail section 41. It will be appreciated that other embodiment of the chamber portion 53 are also within the scope of the present invention.

Additionally or alternatively, the support member 51 can be provided with one or more slot portions 55 extending longitudinally on the circumference of the support member 51. In an exemplary embodiment, each slot portion 55 can be formed to communicate with one chamber portion 53, such as to allow a shaft section 41 to expand from the chamber portion 53 into the corresponding slot portion 55. In another exemplary embodiment, each slot portion 55 can be formed to allow a shaft member 41 to expand away from the support member 51, such as to anchor onto the wall of an intramedullary canal 4. It will be appreciated that other embodiment of the slot portion 55 are also within the scope of the present invention.

When using the fixation device 1 or nail-tube assembly 40, the support member 51 can be introduced into the intramedullary canal 4, such as using an antegrade or a retrograde technique. In an exemplary embodiment, each nail section 41 can be inserted into a chamber portion 53. When the nail sections 41 are warmed up to the body temperature after insertion, one or more fixation members 2 formed on the nail sections 41 can expand outward until they catch the wall of the inner canal 4. The expanded fixation members 2 are capable of securing the fixation device 1 at a predetermined position. If desired, other fasteners, such as locks, screws, pins, wires or the like, can be used to provide additional fixation.

The fixation device 1 can be used to treat various bone fractures. In one exemplary embodiment, such as shown in FIG. 5a and FIG. 5b, the fixation device 1 can be applied to fix a humerus fracture. For example, the entry point can be chosen through the epicondyle 7 to minimize surgical trauma. In an exemplary embodiment, the fixation device 1, while is still retracted and malleable, can be inserted into the humerus through a cavity on either side of the olecranon fossa 9 into the shaft. After the fixation device 1 is seated in the canal 4, the fixation member 2, such as expandable elements 3, can expand to provide the necessary stabilities, such as in FIG. 5b. The expanded parts 2, 3 serve as bone anchors to secure the fixation device 1 at a predetermined position. If desired, other fasteners such as lock screw 36, pin, or wire can be used to provide additional stability to the fixation device. It will be appreciated that various other embodiments of using the fixation device 1 are also within the scope of the present invention.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention.

The presently disclosed embodiments are therefore to be considered in all respects as illustrative and not restrictive.

What is claimed is:

1. A fixation device for use of bone fixation, comprising:
   a nail member having a longitudinal nail length between two nail ends, the nail member having a nail center located at a center of the nail length between the two nail ends; and
   a fixation member formed as a part of the nail member and including the nail center, the fixation member being variable between a first shape and a second shape;
   wherein the nail member can freely move about a fractured bone portion when the fixation member is in the first shape, and
   wherein the fixation member can join to the fractured bone portion and be affixed thereonto for bone fixation in the second shape, whereby the fixation device is mountable to the fractured bone portion and prevented from moving in relation to the fractured bone portion, and
   wherein the fixation member expands longitudinally and transversely in the second shape.

2. The fixation device of claim 1, wherein the fixation member is variable from a flexible state to a rigid state when changing from a retracted shape to an expanded shape.

3. The fixation device of claim 1, wherein the fixation member maintains a retracted shape before being inserted into a bone canal.

4. The fixation device of claim 1, wherein the fixation member changes its shape in response to a temperature change to and from a body temperature.

5. The fixation device of claim 1, wherein the fixation member changes to an expanded shape when being subjected to a body temperature.

6. The fixation device of claim 1, wherein the fixation member changes to a retracted shape when being subjected to a temperature below a body temperature.

7. The fixation device of claim 1, comprising one or more section elements formed on end portions of the nail member and expandable in a transverse direction of the nail member.

8. The fixation device of claim 7, wherein the one or more section elements contract in a longitudinal direction of the nail member to provide a compressing force to a fractured bone portion.

9. The fixation device of claim 1, wherein the fixation member comprises a spiral element expandable both longitudinally and transversely.

10. The fixation device of claim 1, wherein the fixation member is made of a shape memory material.

11. The fixation device of claim 1, wherein the fixation member is made of a nickel-titanium alloy.

12. The fixation device of claim 1 further comprising a section element formed as a part of an end portion of the nail member, wherein the section elements can expand to secure the nail member inside a canal portion.

13. The fixation device of claim 1 further comprising a compressing member for providing an intraosseous force over a fractured bone portion.

14. The fixation device of claim 1 further comprising a support member, which comprises a through chamber portion for accommodating the nail member.

15. The fixation device of claim 1 further comprising one or more fastening members to provide additional fixation.

16. The fixation device of claim 15, wherein the fastening members are bone screws.

17. The fixation device of claim 15, wherein the fastening members are fastening wires.

18. The fixation device of claim 1, wherein the fixation member comprises a spiral element expandable longitudinally.

19. The fixation device of claim 1, wherein the fixation member comprises a spiral element expandable transversely.

20. The fixation device of claim 1, wherein the fixation member is capable of expanding in a longitudinal direction.

21. The fixation device of claim 1 further comprising one or more fastening members to provide additional fixation at end portions of the nail member.

22. The fixation device of claim 1, wherein the fixation member is formed in a middle portion of the nail member.

* * * * *